(12) United States Patent
Lin et al.

(10) Patent No.: US 8,182,540 B2
(45) Date of Patent: May 22, 2012

(54) SKULL ENDOSSEOUS IMPLANT

(75) Inventors: Chou-Ching Lin, Tainan (TW);
Ming-Shaung Ju, Tainan (TW);
Chia-Chu Chiang, Kaohsiung (TW)

(73) Assignee: National Cheng Kung University (TW)

( * ) Notice: Subject to any disclaimer, the term of this patent is extended or adjusted under 35 U.S.C. 154(b) by 465 days.

(21) Appl. No.: 12/079,859

(22) Filed: Mar. 28, 2008

(65) Prior Publication Data
US 2009/0248165 A1  Oct. 1, 2009

(51) Int. Cl.
*A61F 2/02* (2006.01)
*A61F 7/00* (2006.01)
*A61K 9/22* (2006.01)
*A61N 1/00* (2006.01)

(52) U.S. Cl. .......... 623/17.19; 604/891.1; 607/116; 607/45; 607/2

(58) Field of Classification Search ............ 623/17.19; 604/21, 891.1; 607/45, 115, 116, 118, 120, 607/139
See application file for complete search history.

(56) References Cited

U.S. PATENT DOCUMENTS

| | | | | |
|---|---|---|---|---|
| 5,562,670 A | * | 10/1996 | Br.ang.nemark | 606/32 |
| 6,044,304 A | * | 3/2000 | Baudino | 607/116 |
| 7,004,948 B1 | * | 2/2006 | Pianca et al. | 606/129 |
| 7,421,297 B2 | * | 9/2008 | Giftakis et al. | 607/45 |
| 2002/0138068 A1 | * | 9/2002 | Watson et al. | 604/891.1 |
| 2005/0075680 A1 | * | 4/2005 | Lowry et al. | 607/45 |
| 2009/0088826 A1 | * | 4/2009 | Bedenbaugh | 607/116 |

* cited by examiner

*Primary Examiner* — William Matthews
*Assistant Examiner* — Marcia Hoffman
(74) *Attorney, Agent, or Firm* — Bacon & Thomas, PLLC

(57) ABSTRACT

Disclosed is a skull endosseous implant adapted to be implanted in the subject's skull to provide an access channel. A variety of sensor means may be installed in the access channel for monitoring the intracranial status of the subject. The present invention further provides a kit containing the skull endosseous implant.

7 Claims, 12 Drawing Sheets

SKULL ENDOSSEOUS IMPLANT

FIELD OF THE INVENTION

This invention relates to a skull endosseous implant adapted to be implanted in the subject's skull to provide an access channel for receiving sensor means in order to monitor the intracranial status of the subject.

BACKGROUND OF THE INVENTION

In modern medical treatment, occasionally, it is necessary to sense an intracranial status of a subject for different purposes, such as measuring the intracranial pressure or monitoring the brain waves of the subject. Presently, there are several ways to conduct intracranial monitoring. For example, the skull of the subject may be operated to create a temporary opening for inserting an apparatus for measuring. Furthermore, a micro-sensor or a micro-actuator may be implanted inside the skull of the subject for sensing.

However, if the intracranial status monitoring becomes unnecessary or the subject should like to temporarily cease the intracranial status monitoring, the implanted micro-sensors must be removed by another surgical operation on the skull. Furthermore, if the sensing need reoccurs, another round of surgical operations is unavoidable.

SUMMARY OF THE INVENTION

Therefore, it is an object of the present invention to provide a kit capable of providing an access channel extending from the exterior surface to the interior surface of the skull of the patient such that a variety of sensor means may be installed in the access channel for monitoring the intracranial status of the patient.

It is a further objective of the present invention to provide a kit for sensing the intracranial status of a subject.

To achieve the above listed and other objects, the present invention provides a skull endosseous implant, a cover element and an elastic ring-shaped seal member. The skull endosseous implant of the present invention is adapted to be implanted in the subject's skull to provide an access channel. A variety of sensor means may be installed in the access channel for monitoring the intracranial status of the patient. If the intracranial status monitoring becomes unnecessary or the subject should like to temporarily cease the intracranial status monitoring, the sensor means can be removed and the cover element and the elastic ring-shaped seal member may be mounted in the skull endosseous implant to seal the access channel. Thereafter, if the sensing need reoccurs, the cover element and the seal member may be removed to allow the installation of a suitable sensing means again.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1A:
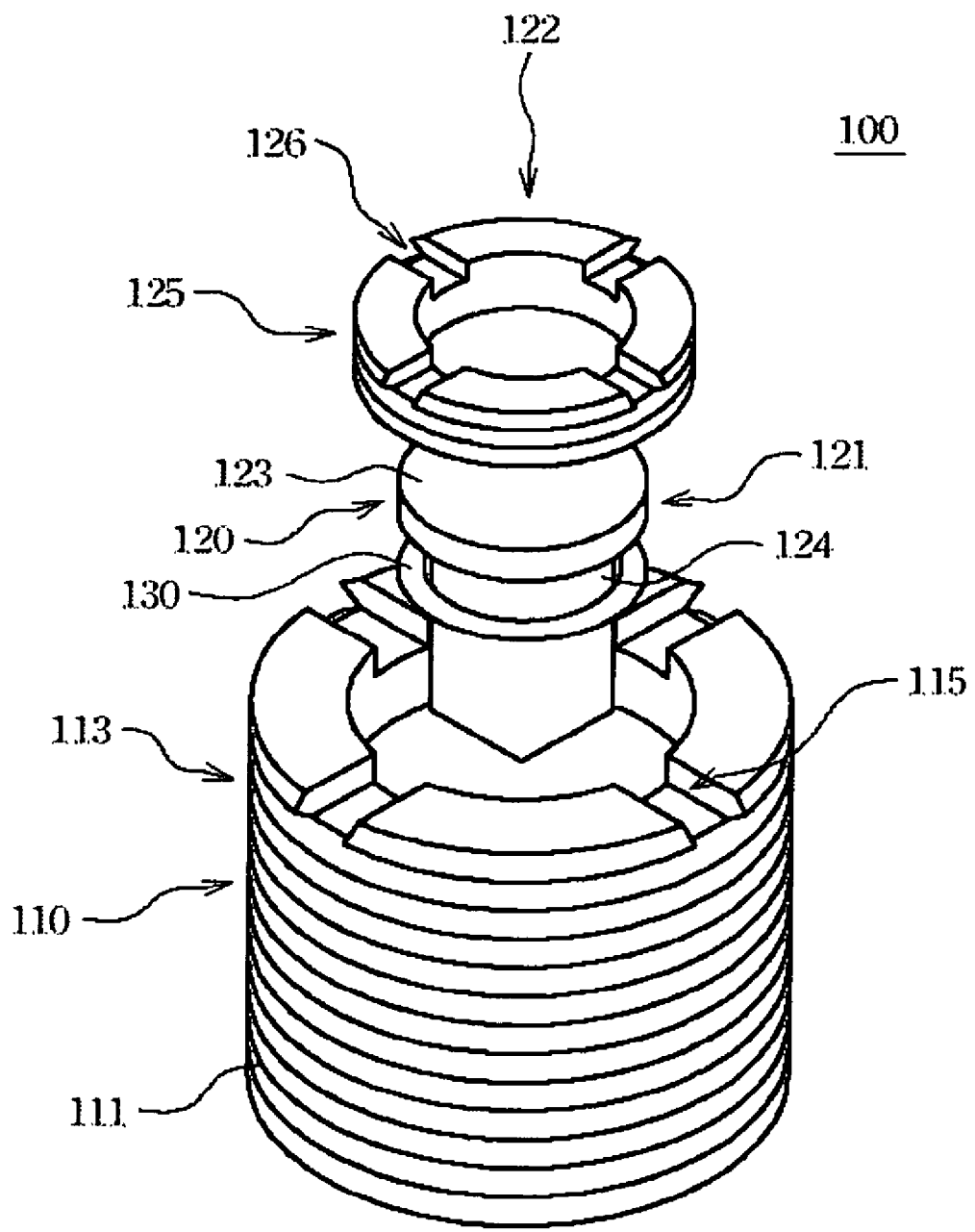
FIG. 1A is a perspective view showing a kit for providing an access channel extending through the skull of a subject according to one embodiment of the present invention.
Figure 1B:
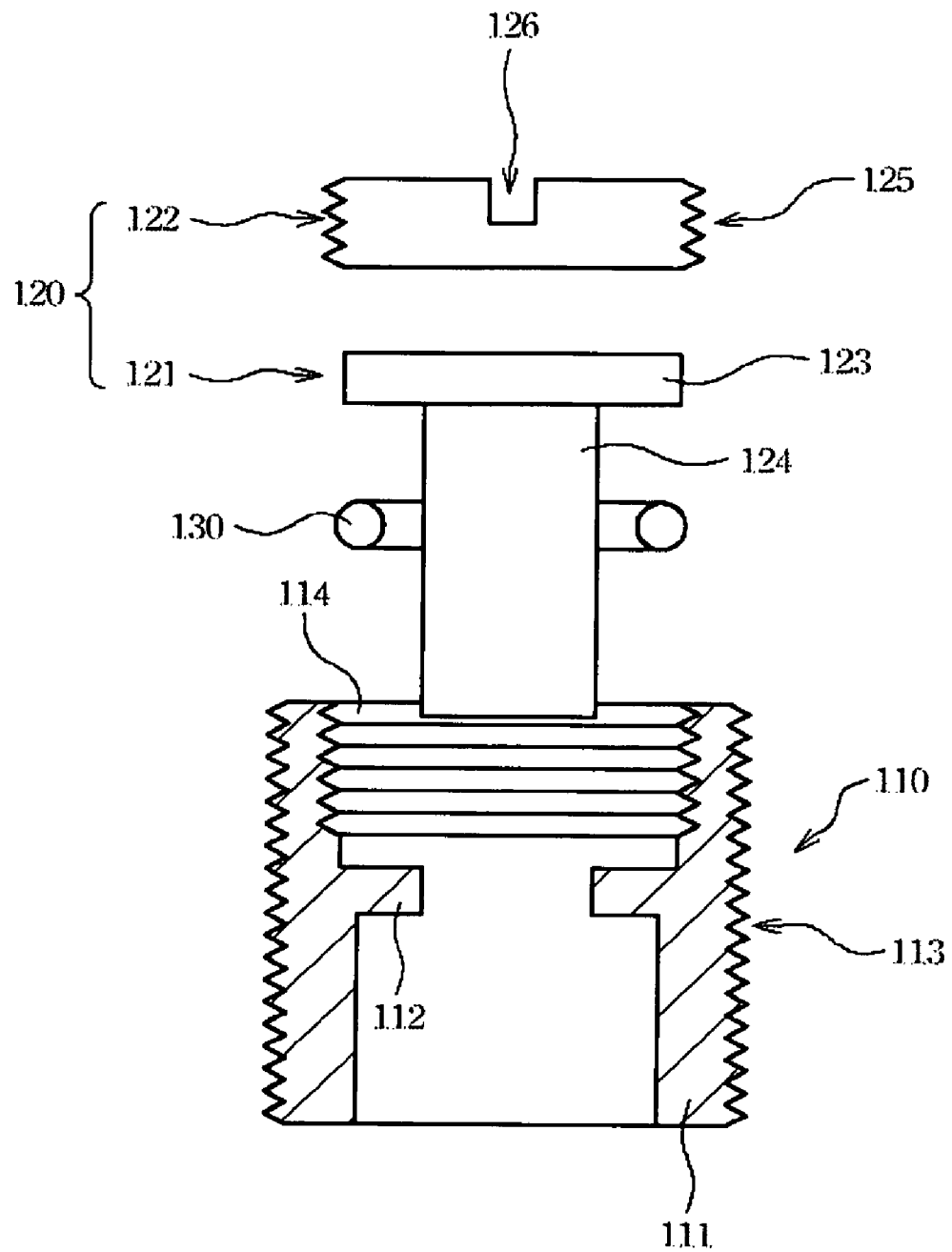
FIG. 1B is a cross-section view showing the kit of FIG. 1A.

Referring first to FIGS. 1A and 1B, a kit for providing an access channel extending through the skull of a subject or a patient is indicated generally at 100. As used herein, the term "subject" or "patient" are used to denote the individual being treated by the kit. It may be a healthy or a sick human being or even an animal. The kit 100 has a plurality of components which are preferably contained within several pockets of a container (not shown), which may be a plastic pouch or envelope or the like. The kit 100 mainly includes a skull endosseous implant 110, a cover element 120 and an elastic ring-shaped seal member 130. The endosseous implant 110 is adapted for implantation into a subject's skull. As best shown in FIG. 1B, the skull endosseous implant 110 includes a hollow cylindrical main body 111 and a protrusion 112 formed inside the hollow cylindrical main body 111. The skull endosseous implant 110 is preferably formed of titanium or titanium alloy and is then coated with hydroxyapatite (HA) or other material that is biocompatible with bone and promotes the growth of bone around it. The skull endosseous implant 110's exterior surface may also be plasma-sprayed titanium. The cover element 120 of the present invention may include a plug 121 and a nut 122 adapted to be screwed into the endosseous implant 110 for fixing the plug 121 to the skull endosseous implant 110. Alternatively, the cover element 120 of the present invention may be a cover screw (not shown). The cover element 120 of the present invention is preferably made of biocompatible material and has high rigidity. The plug 121 may has an enlarged head portion 123 and a shank portion 124 configured to be received in the hollow cylindrical main body 111. The nut 122 has a plurality of external threads 125 to engage internal threads 114 formed in the hollow cylindrical main body 111. A notch 126 is formed at on end of the nut 122 to allow a screw tool (not shown) to screw the nut 122 into the hollow cylindrical main body 111. In this embodiment, the shank portion 124 is in the form of a rectangular shape corresponding to the rectangular hole defined by the protrusion 112 of the skull endosseous implant 110 (see FIG. 2). The elastic ring-shaped seal member 130, preferably made of biocompatible and elastic material, is configured to be disposed between the cover element 120 and the protrusion 112 of the skull endosseous implant 110.

Figure 2:
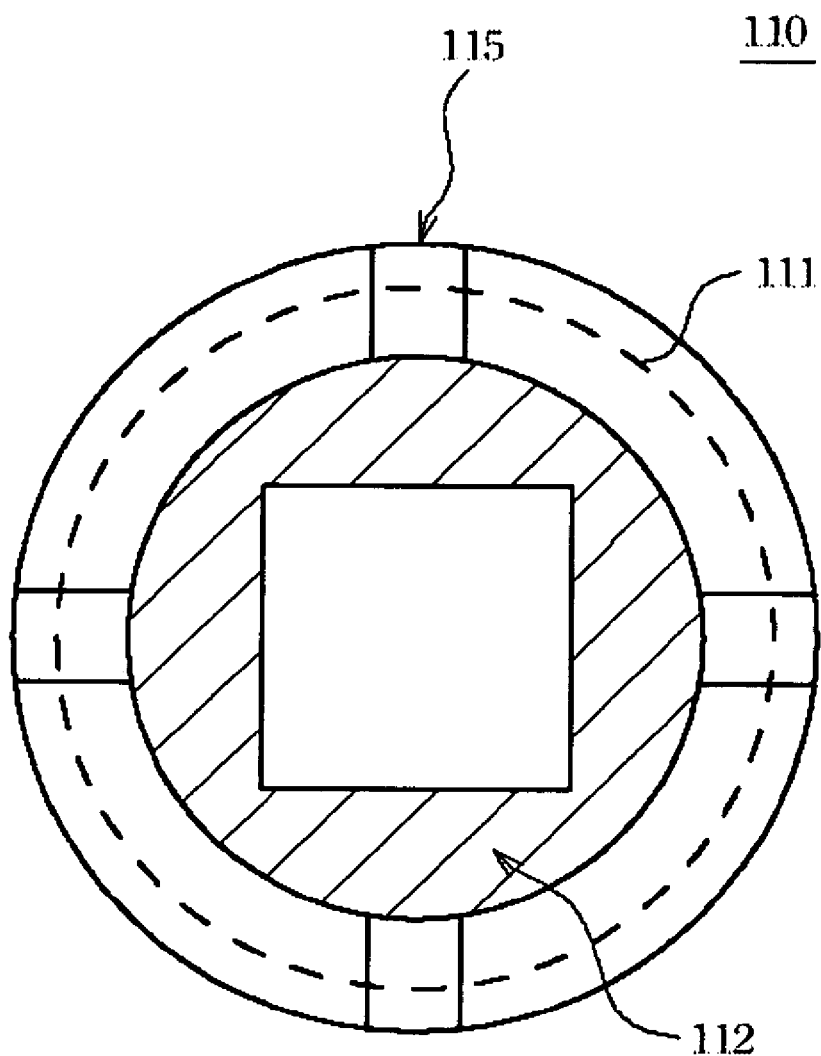
FIG. 2 is a top view showing a skull endosseous implant according to one embodiment of the present invention.
Figure 3:
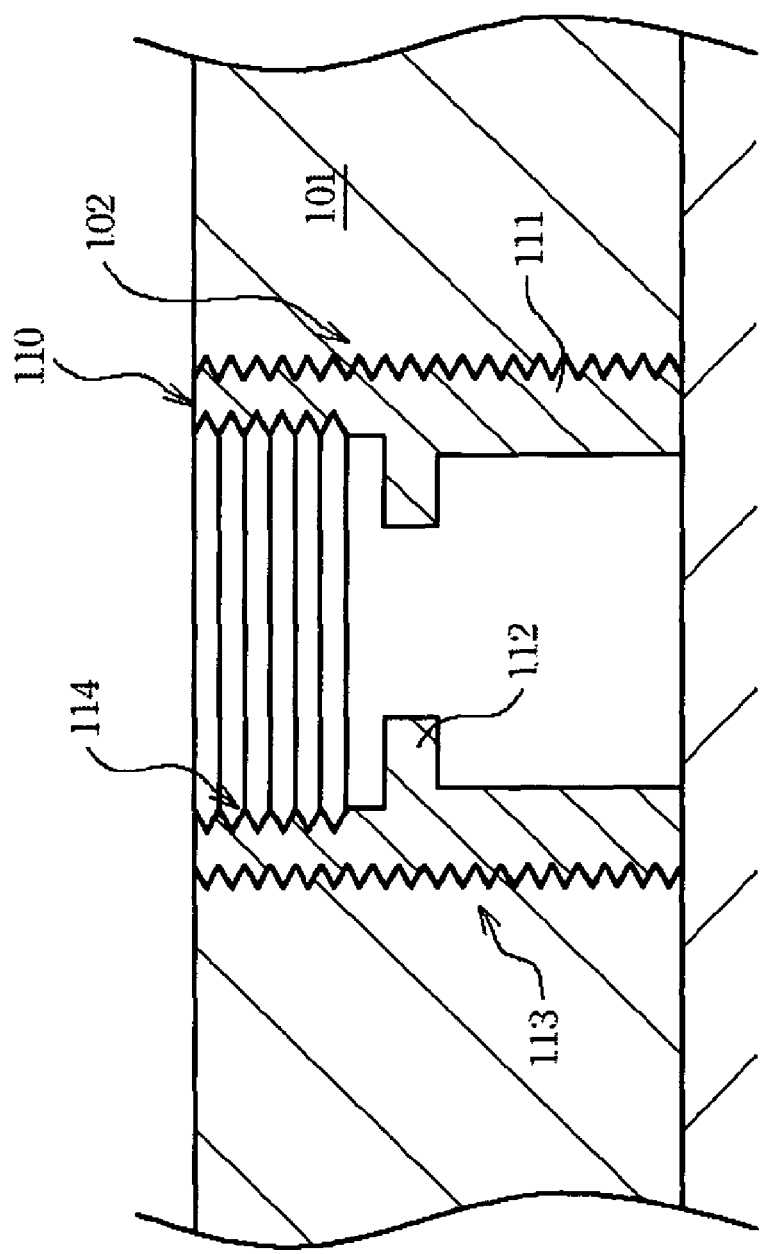
FIG. 3 is a cross-section view showing the skull endosseous implant of FIG. 2 implanted in the subject's skull.
Figure 4:
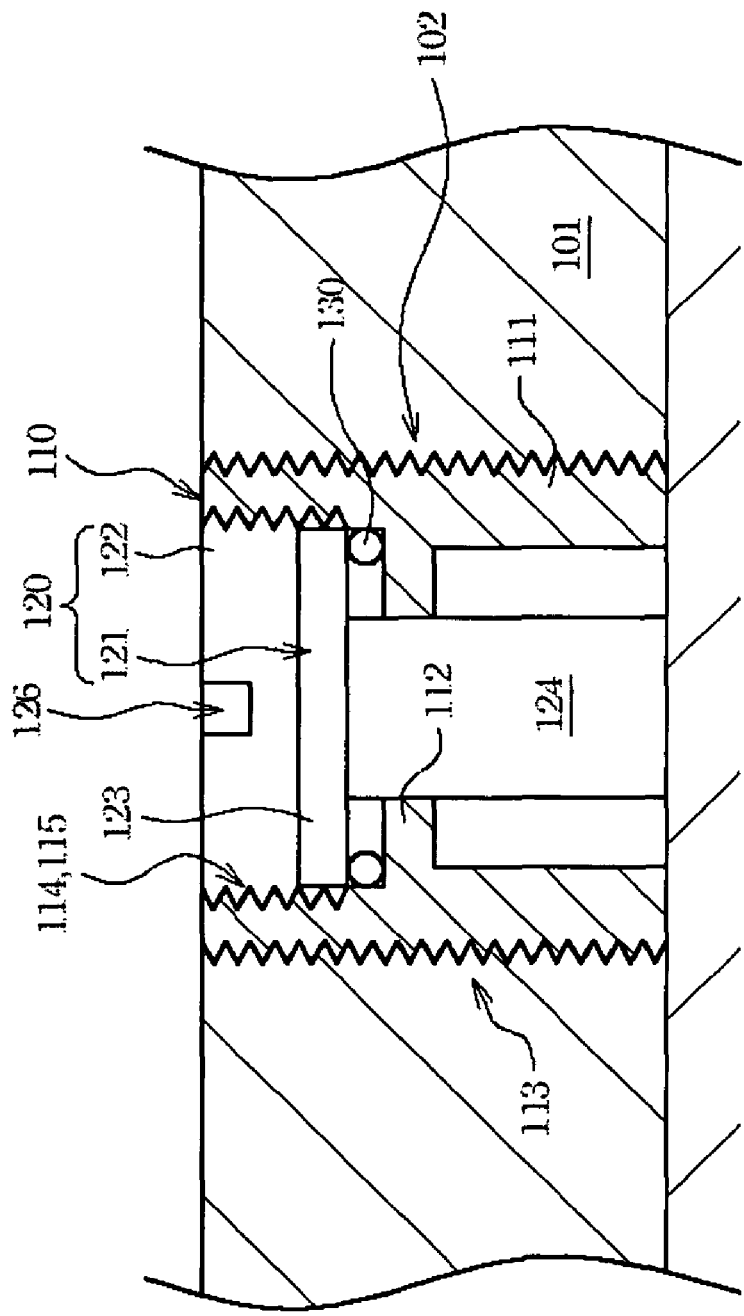
FIG. 4 is a cross-section view showing the kit of FIG. 1 installed in the subject's skull.

FIG. 3 shows the skull endosseous implant 110 of the present invention implanted in the skull 101 of a subject to provide an access channel extending from the exterior surface to the interior surface of the skull 101. As shown, the hollow cylindrical main body 111 has a plurality of external threads 113 to fit into a canal 102 previously made in the subject's skull 101. As best shown in FIG. 2, a plurality of notches 115 are formed at one end of the hollow cylindrical main body 111, thereby allowing a screw tool (not shown) to screw the hollow cylindrical main body 111 into the subject's skull. A variety of sensor means may be installed in the access channel for monitoring the intracranial status of the patient, e.g., the intracranial pressure, the electrocorticography (ECoG), or glucose (or oxygen) concentration in cerebrospinal fluid. Thereafter, if the intracranial status monitoring becomes unnecessary or the subject should like to temporarily cease the intracranial status monitoring, the sensor means can be removed and the cover element 120 and the elastic ring-shaped seal member 130 may be mounted in the skull endosseous implant 110 to seal the access channel. An annular protrusion 112 is provided inside the hollow cylindrical main body 111 to support the elastic ring-shaped seal member 130. As best shown in FIG. 4, when the nut 122 is threaded to engage the internal threads 114 formed in the skull endosseous implant 110, the nut 122 forces the elastic ring-shaped seal member 130 into close contact with the protrusion 112, thereby preventing cerebrospinal fluid loss from the interior to the exterior of the skull 101 of the subject. Note that, if the sensing need reoccurs, the cover element 120 and the seal member 130 may be removed to allow the installation of a suitable sensing means again.

Although the present invention can be used for other applications requiring permanent long term stable access channel through the skull, the following describes an exemplary application where a sensor means is installed in the access channel for monitoring the electrocorticography (ECoG).

Figure 5:
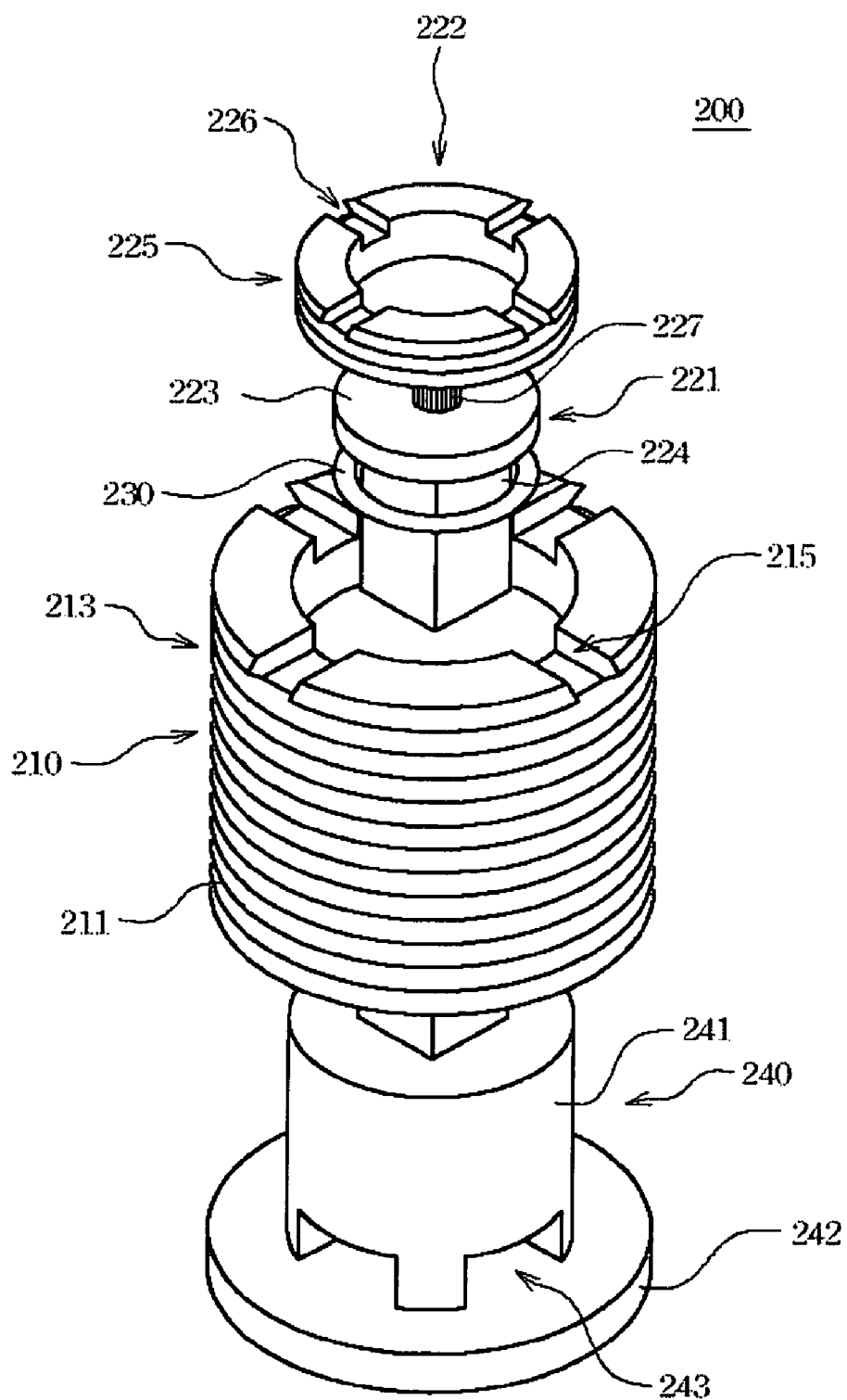
FIG. 5 is a perspective view showing a kit for sensing the electrocorticography (ECoG) of a subject according to one embodiment of the present invention.

Referring to FIG. 5, a kit for sensing the electrocorticography (ECoG) of a subject is indicated generally at 200. The kit 200 mainly includes a skull endosseous implant 210, a connection plug 221, a hollow nut 222, an elastic ring-shaped seal member 230, a guiding tube 240, and a flexible circuit film 250 (see FIG. 6). The skull endosseous implant 210 is substantially similar to the skull endosseous implant 110 (FIGS. 1A and 1B), and will not be described hereinafter in further detail. The hollow nut 222 has external threads 225 and notches 226.

As shown in FIG. 5, the guiding tube 240, preferably made of biocompatible and elastic material, such as silica gel, has a hollow shank portion 241 configured for inserting into the hollow cylindrical main body 211 of the skull endosseous implant 210. Four guiding holes 243 are formed in the hollow shank portion 241 at a location proximate a base portion 242 of the guiding tube 240. The connection plug 221 has an enlarged head portion 223 with an external terminal 227 and a shank portion 224 configured to be received in the hollow shank portion 241 of the guiding tube 240.

Figure 6:
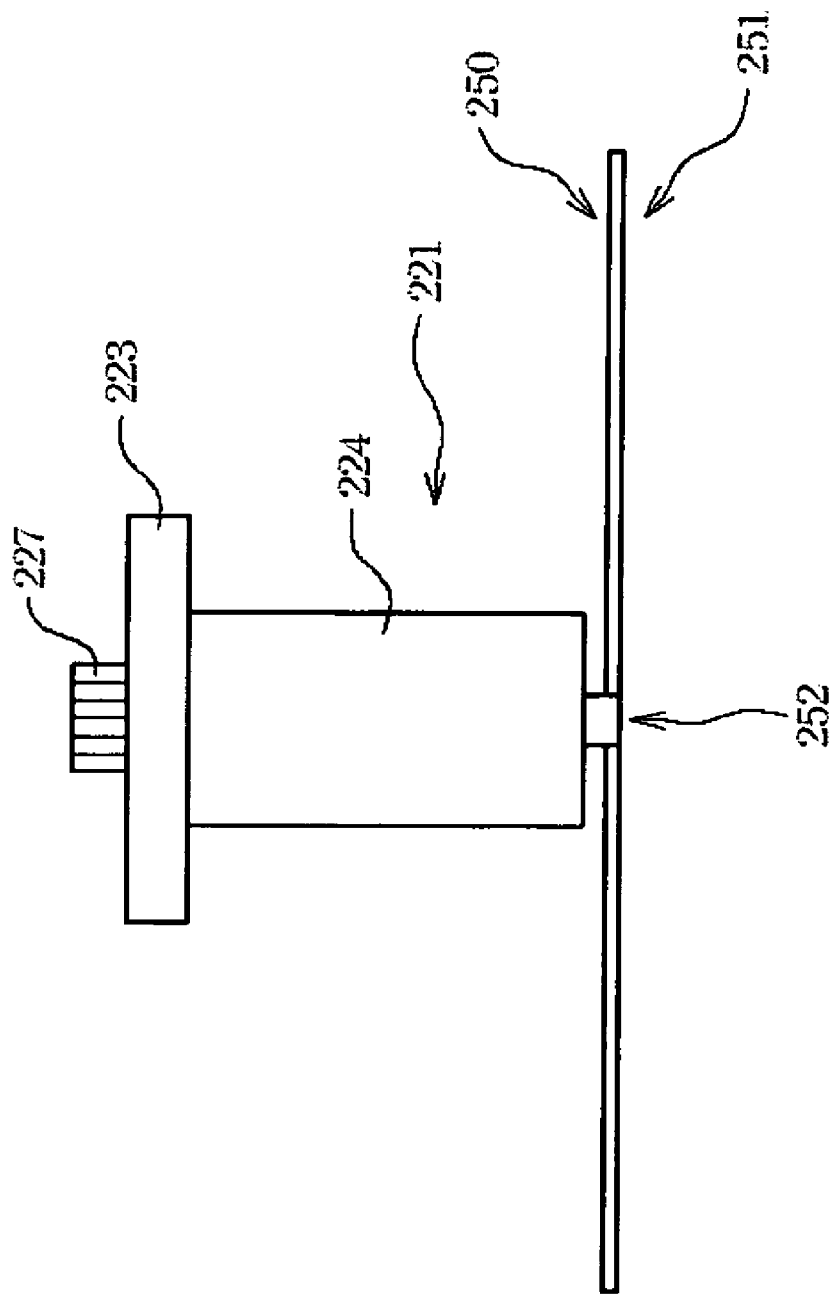
FIG. 6 is a cross-section view showing a connection plug and a flexible circuit film according to one embodiment of the present invention.
Figure 9:
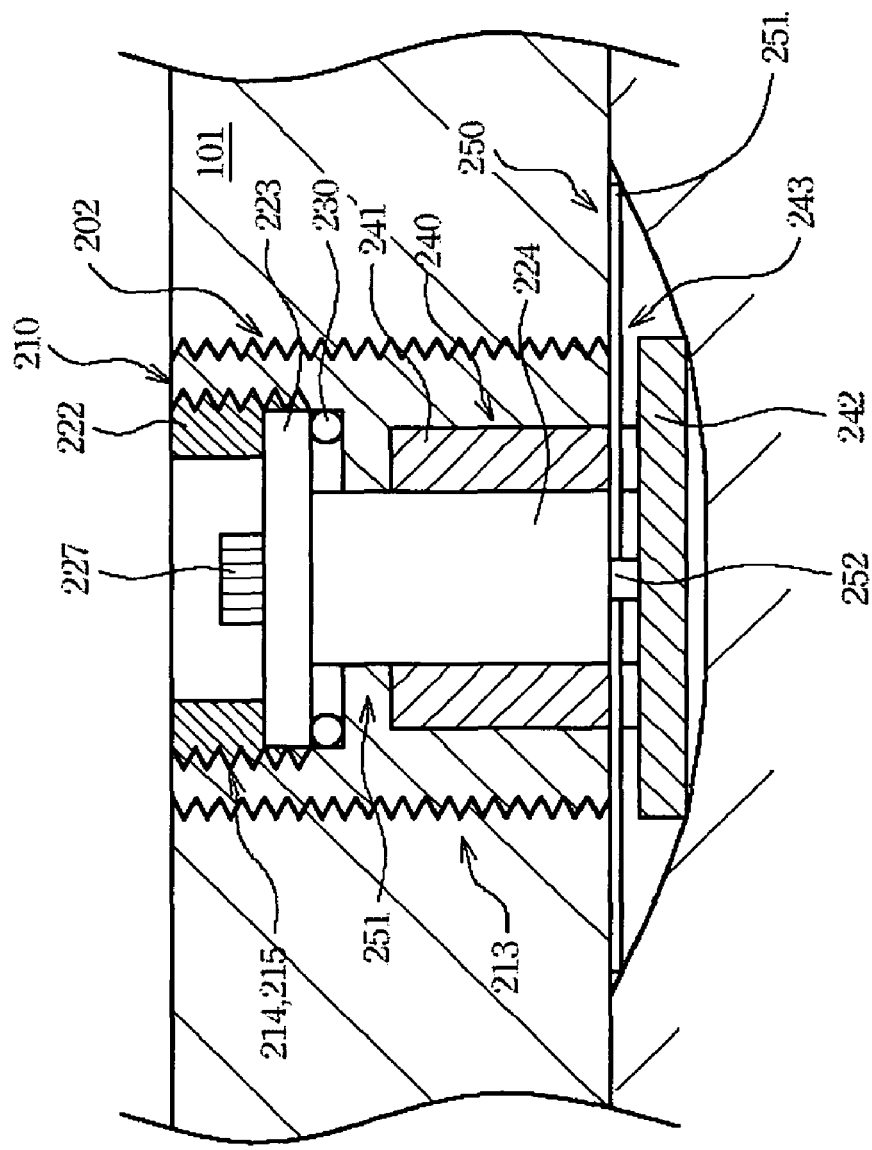

As best shown in FIGS. 6 and 9, one portion 251 of the flexible circuit film 250 (preferably made of high biocompatible and flexible material, such as PI or silica gel) are configured for passing through the guiding holes 243 of the tube 240 to reach the interior of the skull and the other portion 252 thereof are connected to the shank portion 224 of the connection plug 221. The flexible circuit film 250 may include a sensing circuit or a micro-device (such as a micro-sensor or a micro-actuator). In this embodiment, the flexible circuit film 250 includes four sensing electrodes formed on the portion 251 of the flexible circuit film 250 for collecting intracranial EEG signals.

Figure 7:
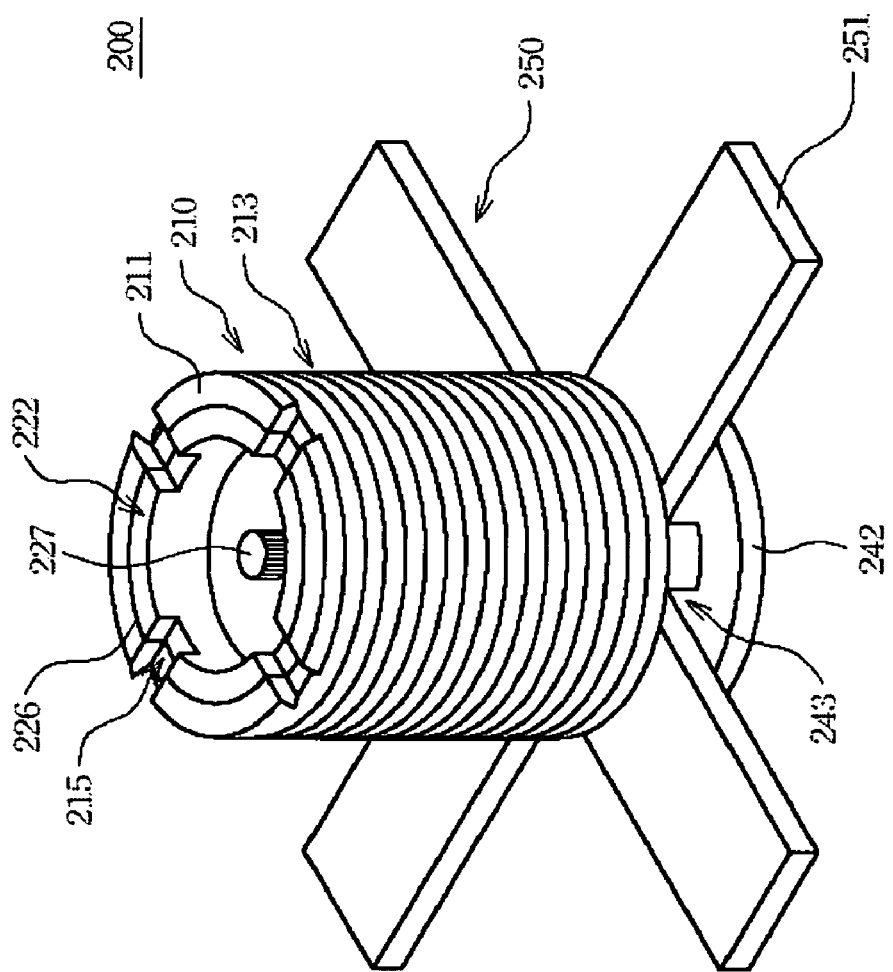
FIG. 7 is a perspective view showing the kit of FIG. 5 in a fully assembled and installed state.

As best shown in FIG. 7, when the connection plug 221 is fixed to the skull endosseous implant 210 by the hollow nut 222, the external terminal 227 of the connection plug 221 is exposed from the hollow nut 222 for electrical connection with an external circuit (not shown). In this embodiment, a connector may be used to connect the external terminal 227 to an EEG monitor. The ECOG sensing kit of the present invention provides a higher signal-to-noise ratio than conventional scalp EEG recording devices. Furthermore, the flexible circuit film 250 of the present invention is formed in a crisscross pattern and the aforementioned sensing electrodes (not shown) are provided on the four terminal portions 251 of the flexible circuit film 250 thereby further enhancing signal-to-noise ratio. When sensing the intracranial status inside the skull 101 of the subject, the flexible circuit film 250 is held by the enlarged base portion 242 of the guiding tube 240, and the four terminal portions 251 of the flexible circuit film 250 extend horizontally to reach the interior of the skull 101 for providing a better EEG sensing sensitivity.

Figure 8:
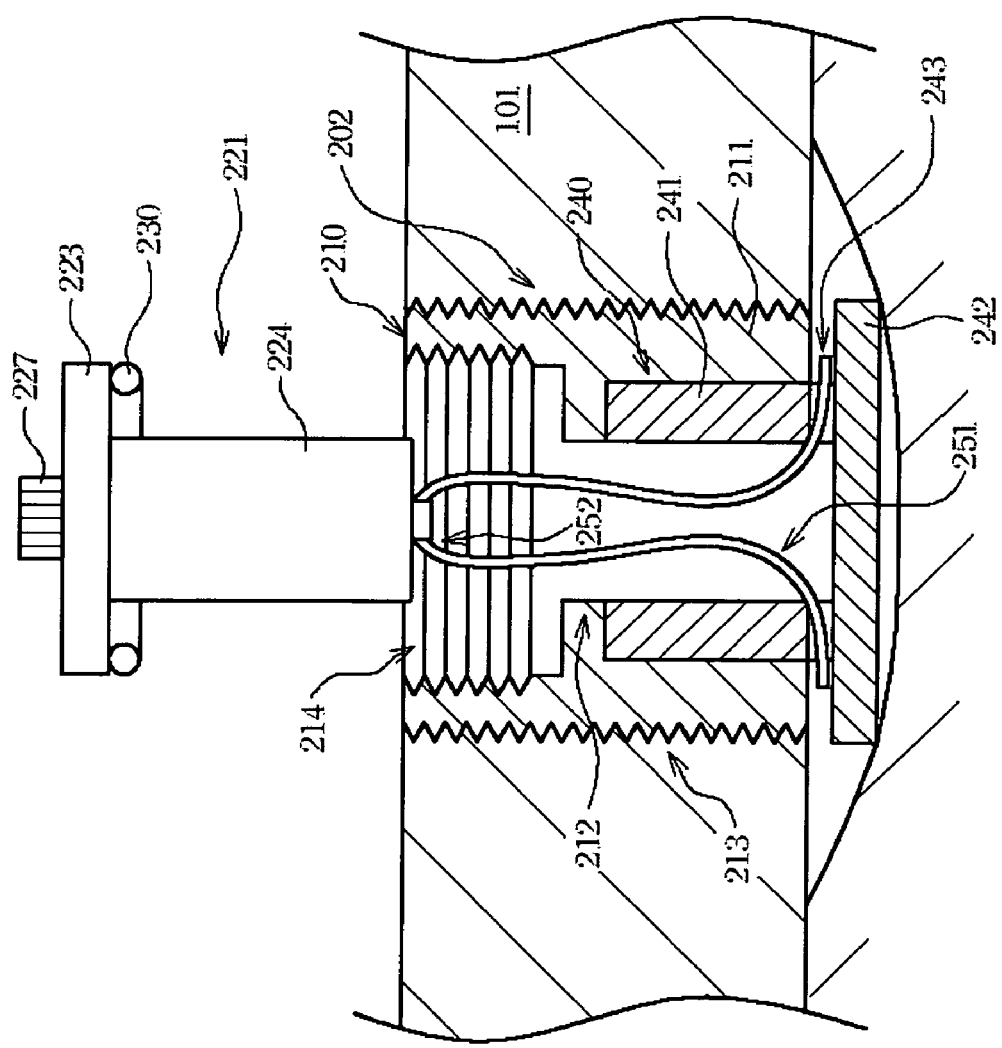
FIG. 8 and FIG. 9 are cross-section views illustrating the installation of the kit of FIG. 5.

Note that the connection plug 221 and the flexible circuit film 250, the elastic ring-shaped seal member 230, and the guiding tube 240 may be installed in the hollow cylindrical main body 111 of the skull endosseous implant 110 as a unit in advance. In the pre-installed unit, the four terminal portions 251 of the flexible circuit film 250 pass through the guiding holes 243 but not extend out of the enlarged base portion 242 of the guiding tube 240 (see FIG. 8) thereby avoiding interfering the implantation of the whole unit in the subject's skull. Thereafter, the pre-installed unit is implanted in the canal 102 of the skull 101 of the subject as previously described. Finally, the connection plug 221 is fixed to the skull endosseous implant 210 by the hollow nut 222, and the four terminal portions 251 of the flexible circuit film 250 extend out of the guiding tube 240 into the space created between the skull 101 and the dura.

Figure 10:
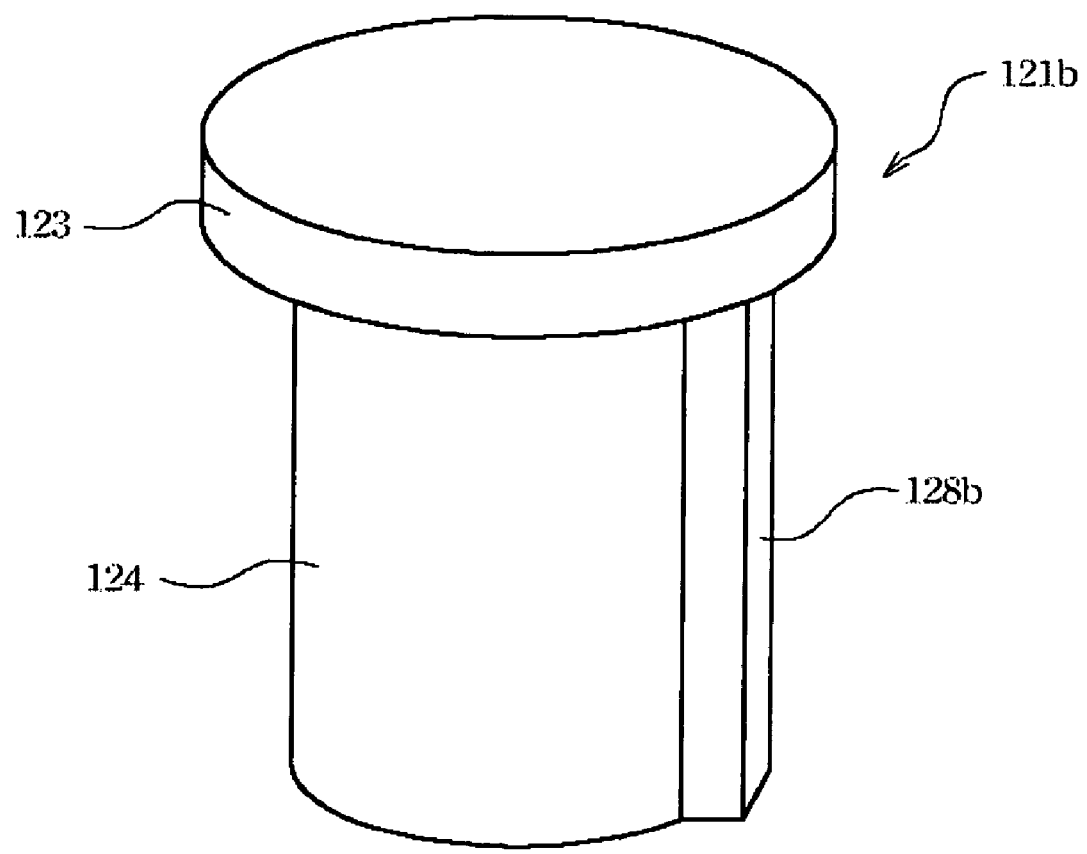
FIG. 10 is a perspective view showing a connection plug according to another embodiment of the present invention.
Figure 11:
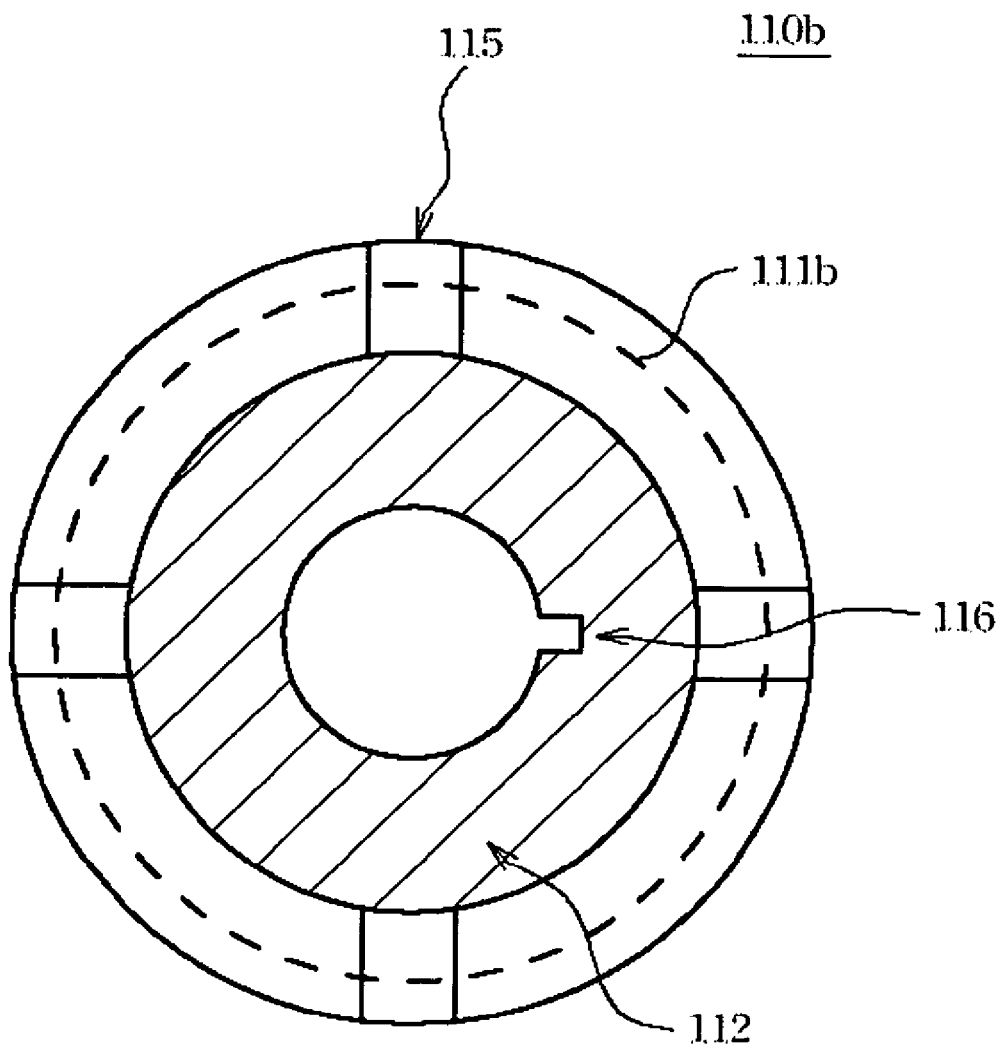
FIG. 11 is a top view showing a skull endosseous implant according to another embodiment of the present invention.

FIG. 10 is a perspective view showing a connection plug 121b according to another embodiment of the present invention. FIG. 11 is a top view showing a skull endosseous implant be used in conjunction with the connection plug 121b of FIG. 10. The connection plug 121b is formed in a cylindrical shape and has a position protrusion 128b formed on the shank portion 124 thereof. As shown in FIG. 11, the protrusion 112 of the hollow cylindrical main body skull 111b of the endosseous implant has a recess 116 formed corresponding to the position protrusion 128b thereof. Therefore, when the connection plug 121b is inserted into the hollow cylindrical main body 111b of the skull endosseous implant 110b, the position protrusion 128b is received in the recess 116, and the connection plug 121b may not rotate with the nut 122 when the nut 122 is being screwed in or out.

As is understood by a person skilled in the art, the foregoing embodiments of the present invention are strengths of the present invention rather than limiting of the present invention. It is intended to cover various modifications and similar arrangements included within the spirit and scope of the appended claims, the scope of which should be accorded the broadest interpretation so as to encompass all such modifications and similar structures.

What is claimed is:

1. An electrocorticography sensing skull endosseous implant for sensing an intracranial status of a skull of a subject, wherein the skull endosseous implant comprises:

a hollow cylindrical main body with a plurality of external threads to fit into a canal previously made in the skull of the subject and a plurality of internal threads formed inside the hollow cylindrical main body;

a protrusion formed on an inner side surface of the hollow cylindrical main body and extending from the inner side surface of the hollow cylindrical main body;

a guiding tube configured for inserting from a bottom side of the hollow cylindrical main body, wherein the guiding tube has a hollow shank portion configured for inserting into the hollow cylindrical main body and an enlarged base portion, the guiding tube having at least one guiding hole formed in the hollow shank portion at a location proximate the base portion thereof;

a connection plug configured for inserting from an upper side of the hollow cylindrical main body, wherein the connection plug has an enlarged head portion with an external terminal and a shank portion configured to be received in the hollow shank portion of the guiding tube, and the connection plug is made of biocompatible material with high rigidity;

a hollow nut for engagement with the internal threads of the hollow cylindrical main body and fixing the connection plug to the hollow cylindrical main body;

an elastic ring-shaped seal member configured to be disposed between the enlarged head portion of the connection plug and the protrusion, wherein, when the connection plug is fixed to the hollow cylindrical main body, the elastic ring-shaped seal member is forced by the enlarged head portion of the connection plug into close contact with the protrusion thereby preventing cerebrospinal fluid loss from an interior to an exterior of the skull of the subject, and the external terminal of the connection plug is exposed from the hollow nut for electrical connection with an external circuit; and a flexible circuit film having a first portion configured for passing through the at least one guiding hole to reach the interior of the skull and a second portion connected to the shank portion of the connection plug, wherein the flexible circuit film is formed from a thin film in a crisscross pattern and used for collecting intracranial electroencephalogram signals.

2. The skull endosseous implant as claimed in claim 1, wherein the flexible circuit film is made of biocompatible material.

3. The skull endosseous implant as claimed in claim 1, wherein the hollow cylindrical main body is made of titanium or titanium alloy.

4. The skull endosseous implant as claimed in claim 1, wherein the shank portion of the connection plug is in the form of a noncircular shape.

5. The skull endosseous implant as claimed in claim 1, wherein the shank portion of the connection plug includes a position protrusion formed on the circumference thereof.

6. The skull endosseous implant as claimed in claim 1, wherein the hollow cylindrical main body has at least one first notch formed at one end thereof.

7. The skull endosseous implant as claimed in claim 1, wherein the hollow nut has at least one second notch formed at one end thereof.

\* \* \* \* \*